(12) United States Patent  (10) Patent No.: US 7,665,363 B2
Capilla et al.  (45) Date of Patent: Feb. 23, 2010

(54) ULTRASONIC HEAD FOR PULSE-ECHO MULTICHANNEL INSPECTION

(75) Inventors: Ester Baños Capilla, Alicante (ES); Alvaro Espada Tejedor, Madrid (ES)

(73) Assignee: Airbus Espana, S.L., Madrid (ES)

( * ) Notice: Subject to any disclaimer, the term of this patent is extended or adjusted under 35 U.S.C. 154(b) by 634 days.

(21) Appl. No.: 11/499,359

(22) Filed: Aug. 4, 2006

(65) Prior Publication Data

US 2007/0074573 A1  Apr. 5, 2007

(30) Foreign Application Priority Data

Sep. 30, 2005  (ES) ................................ 200502380

(51) Int. Cl.
    *G01N 29/26* (2006.01)
(52) U.S. Cl. .............................. 73/627; 73/640; 73/644; 73/660
(58) Field of Classification Search .................... 73/627, 73/635, 637, 638, 640, 641, 644, 660
    See application file for complete search history.

(56) References Cited

U.S. PATENT DOCUMENTS

| | | | |
|---|---|---|---|
| 4,112,850 A * | 9/1978 | Sigel-Gfeller | 104/138.2 |
| 4,166,395 A | 9/1979 | Dannehl | |
| 4,774,842 A * | 10/1988 | Kollar et al. | 73/640 |
| 4,862,748 A * | 9/1989 | Woodmansee | 73/641 |
| 5,505,809 A * | 4/1996 | Yamamoto et al. | 156/264 |
| 5,576,492 A | 11/1996 | Phalin | |
| 5,625,148 A * | 4/1997 | Rutherford | 73/618 |
| 6,138,515 A * | 10/2000 | Moufle et al. | 73/639 |
| 6,666,094 B1 * | 12/2003 | Sauerland | 73/618 |
| 7,516,664 B2 * | 4/2009 | Meier et al. | 73/644 |
| 2007/0044564 A1 * | 3/2007 | Bui et al. | 73/618 |
| 2008/0196856 A1 * | 8/2008 | Terada et al. | 164/136 |
| 2009/0064787 A1 * | 3/2009 | Kennedy et al. | 73/634 |

FOREIGN PATENT DOCUMENTS

DE 2945586 5/1981
DE 3033348 4/1982

* cited by examiner

*Primary Examiner*—J M Saint Surin
(74) *Attorney, Agent, or Firm*—Klauber & Jackson L.L.C.

(57) ABSTRACT

Ultrasonic head for pulse-echo multichannel inspection applied to flat and curved surfaces, which is connected to a displacement system (3), and which comprises a chassis (1) housing a tilting frame (4) joined to said chassis via a first point of rotation (1a) and a second point of rotation (1b) which define a main tilting axis (1c) around which the tilting frame (4) rotates, said tilting frame (4) presenting a set of feeler-carriers (2) in its central opening (4h) which carry an array of ultrasonic feelers (12), said array of feel-carriers (2) being able to rotate around at least one axis of rotation (5, 5a, 5b) transverse to the main tilting axis (1c) in an independent movement to that made by the tilting frame (4), the tilting frame (4) being able to be divided into two secondary frames (6, 8) which rotate independently of the rotation of the tilting frame (4).

18 Claims, 9 Drawing Sheets

(A-A')

(B-B')

ULTRASONIC HEAD FOR PULSE-ECHO MULTICHANNEL INSPECTION

CROSS REFERENCE TO RELATED APPLICATIONS

The present application claims priority from Spanish Application Serial No. P200502380, filed on Sep. 30, 2005. Applicants claim priority under 35 U.S.C. § 119 as to the said Spanish application, and the entire disclosure of said application is incorporated herein by reference in its entirety.

TECHNICAL FIELD OF THE INVENTION

The present invention belongs to the technical field of non-destructive inspection of pieces made of composite materials by means of ultrasonic techniques and, more particularly, the present invention refers to a head for multichannel pulse-echo inspection of curved pieces manufactured in composite material of large dimensions used in the field of aeronautics.

STATE OF THE ART PRIOR TO THE INVENTION

Ultrasonic inspection is a process much used for the non-destructive testing of carbon-fibre pieces.

In particular, the technique of ultrasonic pulse-echo inspection is based on the introduction of elastic mechanical waves in the material to inspect, which propagate and undergo phenomena of reflection, refraction, attenuation, diffraction, etc. For adequate transmission of the ultrasonic waves, a coupling medium is needed, such as water for example.

If one has a homogenous material, it will not display any discontinuities in the propagation of the waves; in the event that the material has a defect, then the waves will not be continuous.

The process of pulse-echo inspection used so far has been based on:
  Automatic machines with multiple channels for the inspection of large flat surfaces.
  Single-channel and multi-channel manual systems for inspection of small surfaces.

In machines used to date, the ultrasonic inspection has used rigid heads, which means that their functioning was adequate for flat pieces but curved pieces raised the drawback that this rigid head could not adequately adapt itself to the variations in curvature of the surface to inspect, and therefore the said rigid head did not manage to maintain contact with the surface, thus preventing the correct analysis of the piece.

The system forming the object of the patent application arises out of the need to inspect large curved surfaces used in the field of aeronautics.

DESCRIPTION OF THE INVENTION

The aim of the present invention is to overcome the drawbacks of the mechanisms of the state of the art by means of an ultrasonic head for pulse-echo multichannel inspection. Said invention applies to the non-destructive analysis of large pieces with flat or curved surfaces.

The invention comprises a chassis in which there exists an array of feeler-carrier devices housing the ultrasonic feelers necessary for the analysis. In order to sweep the entire surface of the piece the head has to be displaced, and for this it can be coupled to a displacement system, for example, a machine of the moving-bridge type or of the moving-gantry type. With the said invention, one has sufficient degrees of freedom for ensuring the coupling with the curved surfaces that it is wished to inspect. Said degrees of freedom are achieved thanks to rotations or tiltings and vertical movements made by elements of the chassis.

In the chassis there exists a tilting frame of similar dimensions to those of the chassis. This frame can tilt around the main tilting axis defined by the points at which the frame is attached to the chassis (first point of rotation and second point of rotation). In the central opening defined by the tilting frame are the feeler-carriers, located along the axes of rotation transverse to the main tilting axis of that frame. In this way, two different rotation movements are obtained in order to adapt the position of the feelers to the curvature of the surface to examine.

In one of the embodiments, the points of rotation via which the tilting frame is attached to the chassis are located in a first lower base of said chassis and said first lower base surrounds at least a portion of the tilting frame. In this embodiment, both the tilting frame and the first lower base have a substantially rectangular shape, formed by different cross-members or side-members, with the points of attachment of the tilting frame to the first lower base, which are the first point of rotation and the second point of rotation, being located at opposite points of opposite cross-members. In a preferred embodiment, said points of rotation are located on plates projecting from the first lower base, these plates having a substantially inverted triangular shape, the points of rotation being located in a zone close to the free lower vertex of each of the two plates, which facilitates the rotation of the tilting frame around the main tilting axis and the examination of surfaces with greater variation in height owing to greater curvatures or greater irregularities.

In another embodiment, the tilting frame displays a central cross-member parallel to the main tilting axis, thereby separating the central opening into two parts. In this way, said central opening where the feeler-carriers are housed becomes divided into two independent zones where a set of axes with independent rotation among them can be located where an array of feelers is going to be located, the head being able to be more easily adapted to the variation in the curvature of the piece.

In another embodiment, the division of the central opening of the cross-member is exploited in order to locate separate secondary frames in each of the two parts into which the central opening is divided. Said secondary frames are arranged in secondary tilting axes parallel to the main tilting axis for the tilting frame, said secondary frames being joined to the tilting frame in the same way as the tilting frame is joined to the lower base. In this way, the secondary frames display a rotation movement equal to that of the tilting frame, but independent of the rotation of the latter and independent between both secondary frames. Located in the openings contained in those frames are the feeler-carriers in their respective axes of rotation. So, the adaptability to different curvatures of the surface will be much greater than with a single frame.

The way in which the chassis is attached to the displacement machine is carried out via a second lower base to which is coupled the first lower base. This coupling is achieved by means of adjustment elements which permit vertical displacement of the first lower base with respect to the second lower base. In this way, there exists a vertical degree of freedom, which manages to improve the adaptability of the feelers to the different curvatures of the surfaces without losing contact with them, and without it being necessary for the displacement machine to make major vertical displacements.

In one of the embodiments, these adjustment elements are springs located on some rods joining the first and second base, it being the springs which permit vertical movement when they are compressed or relaxed along the travel of the machine over the piece, actuated by the contact of the head on that piece.

Another possibility of movement in height, though with lesser dimension, is achieved by virtue of means of adjustment in height of the feeler-carriers in such a way that they permit vertical movement of those feeler-carriers so that the latter can be adjusted to minor variations in height or due to irregularities of the surface to test.

In a preferred embodiment, these means of adjustment in height consist of small feeler springs arranged in each of the feeler-carriers.

Owing to the friction existing between the surface of the piece to test and the feeler-carriers in their displacement along that surface, the lower surface of the feeler-carrier can become worn giving rise to a series of problems such as variation in the height of the feeler-carrier and consequent errors in measurement. Therefore, in a preferred embodiment of the invention, the feeler-carrier is divided into two parts, and it is possible to replace the lower part with a new one when said lower part, which is the one that comes into contact with the piece, becomes worn. In this way, one avoids having to replace the entire feeler-carrier when its lower part wears out.

For a proper transmission of the ultrasonic waves, a coupling medium is needed. In this case, the coupling medium used is water. Inlet means for water provide the water needed for the correct transmission of the ultrasonic waves. In a preferred embodiment, said water inlet means consist of an inlet duct for water provided in each of the feeler-carrier devices.

A preferred embodiment of the invention presents an array of end-of-piece detection sensors. The purpose of these sensors is to detect the end of the piece in the movement of the head along the piece to test, thereby preventing the feelers from departing from the surface to test. Said detection sensors are located at the ends of the frame, or of the frames in the event that there are several, as has been stated in some of the embodiments. Said end-of-piece detection sensors can preferably be removed so that they can be used or not depending on the need.

BRIEF DESCRIPTION OF THE FIGURES

Below, in order to facilitate a better understanding of this specification and forming an integral part thereof, a series of drawings are attached in which, by way of illustration only and not limiting, the object of the invention has been represented in some of its different embodiments.

Figure 1:
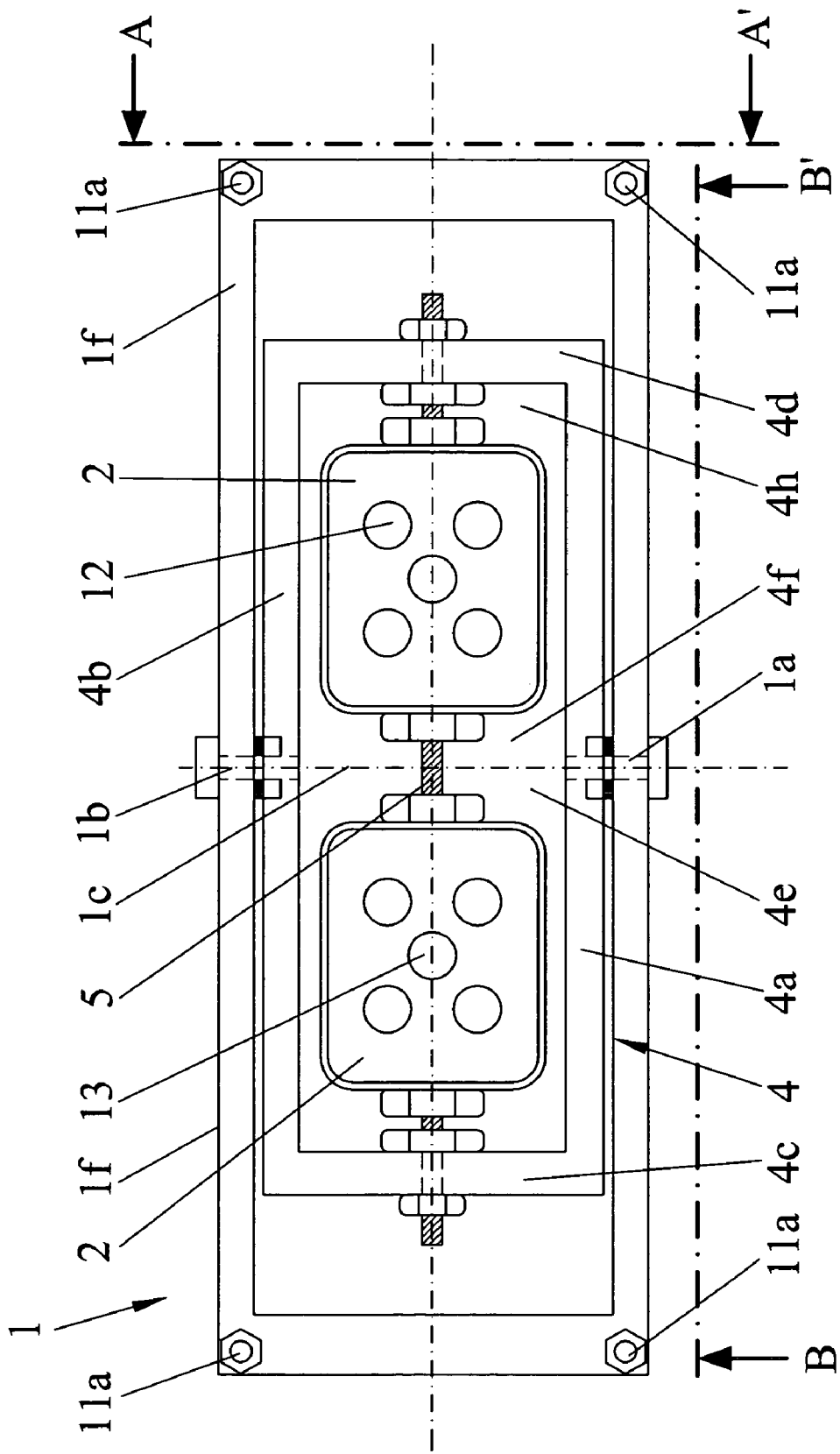
FIG. 1 is a diagrammatic view in lower plan of a head in accordance with a first embodiment of the invention.

Appearing in these figures are numerical references denoting the following elements:

1 chassis
1a first point of rotation
1b second point of rotation
1c main tilting axis
1d first plate
1e second plate
1f first lower base
2 feeler-carrier device
3 displacement system
4 tilting frame
4a first side-member
4b second side-member
4c first end cross-member
4d second end cross-member
4e first part of the central opening
4f second part of the central opening
4g central cross-member
4h central opening
5, 5a, 5b axis of rotation
6 first secondary tilting frame
6a first secondary opening
7 first secondary tilting axis
8 second secondary tilting frame
8a second secondary opening
9 second secondary tilting axis
10 second lower base
11 adjustment elements
11a rod
11b holes
11c spring
12 feeler
13 attachment element between lower and upper part of the feeler-carrier
14 end-of-piece detection sensors
15 water inlet means, water inlet duct
16 upper part of the feeler-carrier
17 lower part of the feeler-carrier
18 means of adjustment in height of feeler-carrier, carrier springs

MODES OF EMBODIMENT OF THE INVENTION

Figure 2:
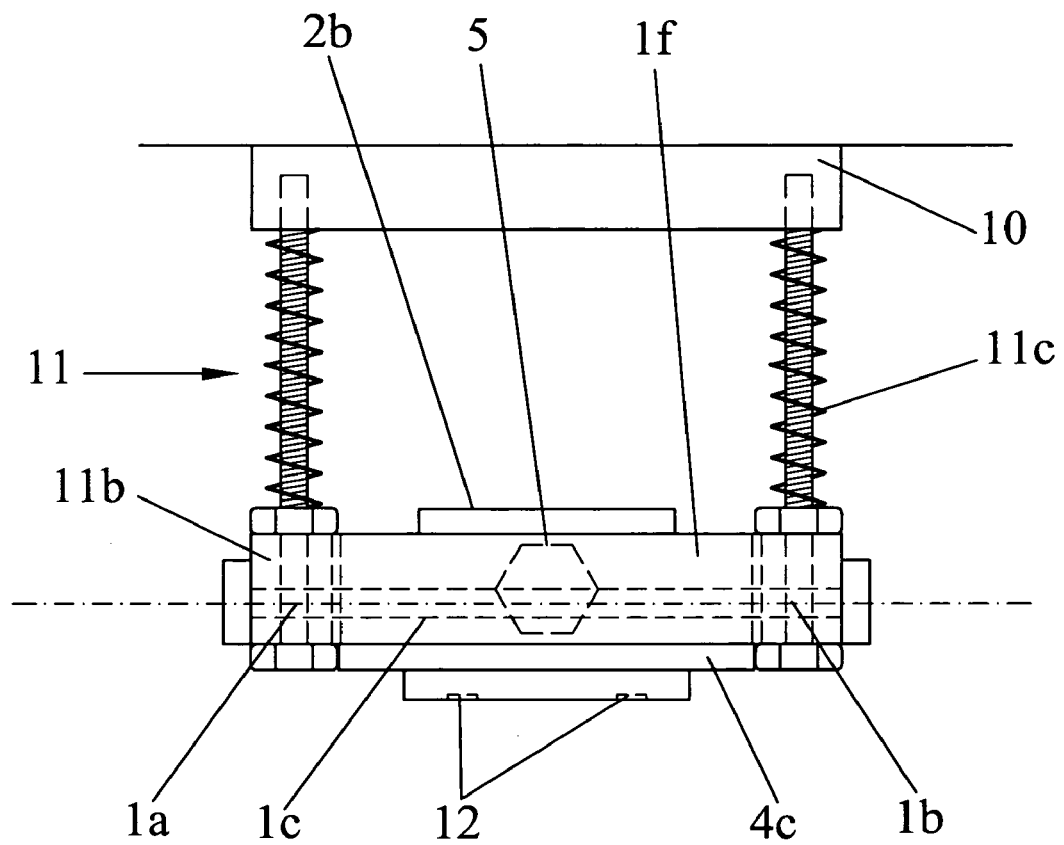
FIG. 2 is a diagrammatic view of the head in elevation along the line A-A' appearing in FIG. 1.
Figure 3:
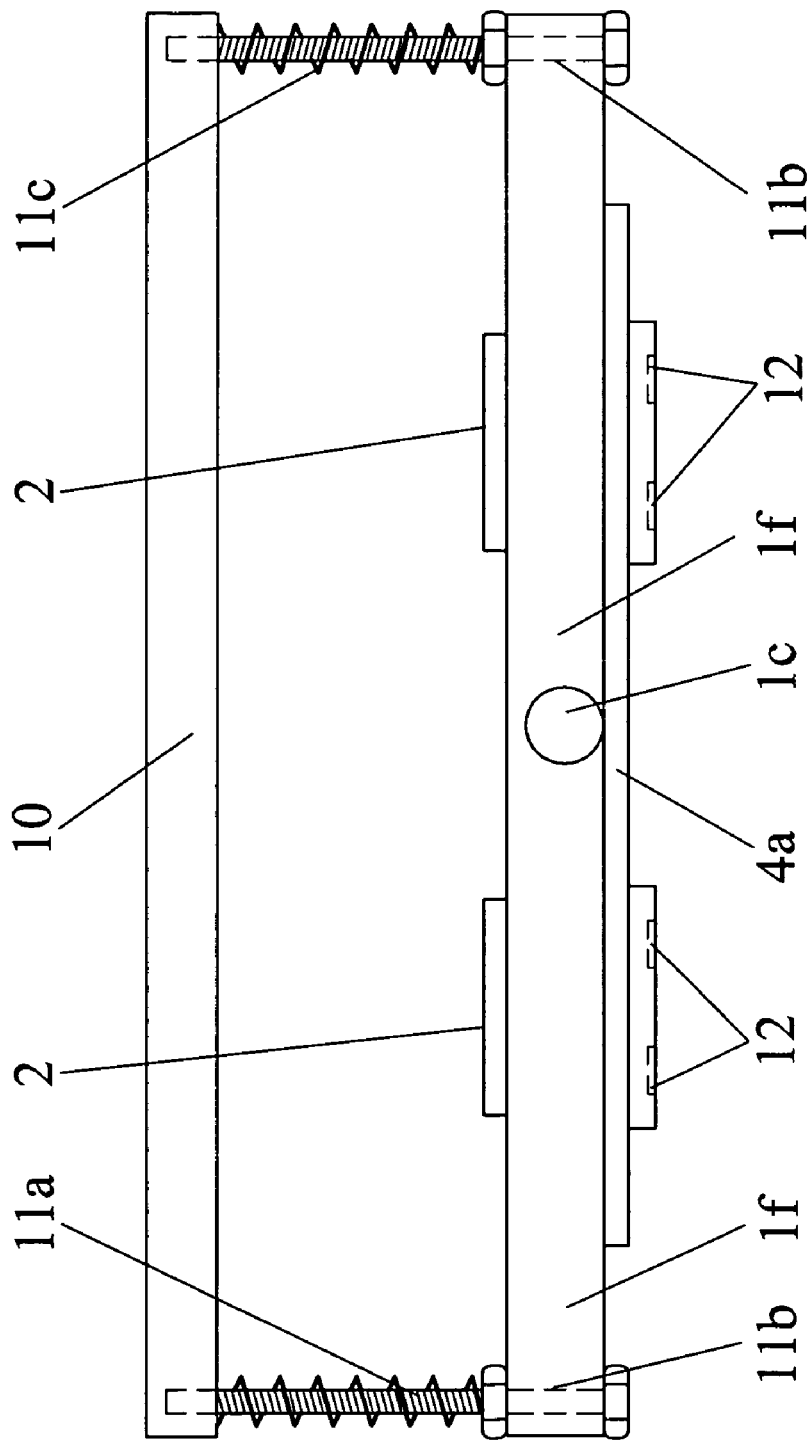
FIG. 3 is a diagrammatic view of the head in elevation along the line B-B' appearing in FIG. 1.

FIGS. 1, 2 and 3 show a first embodiment of the invention. It comprises a chassis 1 housing an array of feeler-carrier devices 2 carrying at least one ultrasonic feeler 12. Said chassis 1 can be coupled to a displacement system 3 which permits the head to be displaced over the entire surface of the pieces to inspect, both curved and flat, by means of ultrasonic sweeping.

Said chassis 1 comprises a first point of rotation 1a and a second point of rotation 1b between which is defined a main tilting axis 1c, and a tilting frame 4 coupled to the chassis 1 via said first point of rotation 1a and said second point of rotation 1b in such a way that said tilting frame 4 rotates around the main tilting axis 1c, and said tilting frame 4 defines a central opening 4h. Located in that central opening 4h is the array of feeler-carriers 2 in at least one axis of rotation 5, 5a, 5b transverse to the main tilting axis 1c of the tilting frame 4, in such a way that said feeler-carrier devices 2 rotate around the axes of rotation 5, 5a, 5b.

FIGS. 1, 2 and 3 show the most general embodiment of this invention, with a single axis of rotation 5, to which are coupled two feeler-carrier devices 2.

The advantage shown by this embodiment compared to those existing in the state of the art is the greater adaptability of the feelers 12 over the surface of the piece to test, being able to adapt themselves to the different variations of curvature of that surface and at all times maintaining contact with it thanks to the possibility of rotation both of the tilting frame 4 around the main tilting axis and of the feeler-carriers 2 around the axes of rotation 5, 5a, 5b.

In FIGS. 1 and 2 it can be seen that the first point of rotation 1a and the second point of rotation 1b are to be found at opposite points of a first lower base 1f, which surrounds at least a portion of the tilting frame 4. In this embodiment, both the tilting frame 4 and the first lower base 1f present a substantially rectangular shape in which the tilting frame 4 comprises a first side-member 4a and a second side-member 4b perpendicular to the main tilting axis 1c, and they are joined together respectively by a first end cross-member 4c and a second end cross-member 4d, which are parallel to the main tilting axis 1c. Said substantially rectangular shape presents the advantage of simple manufacture at the same time as allowing the possibility of various arrangements and number of feeler-carriers to be adapted.

As can be seen in FIG. 1, the first point of rotation 1a and the second point of rotation 1b are to be found at opposite points located on side-members opposing said first lower base 1f, these being parallel to the respective first side-member 4a and second side-member 4b of the tilting frame 4, in such a way that the first lower base surrounds at least the said first side-member 4a and second side-member 4b.

Figure 4:
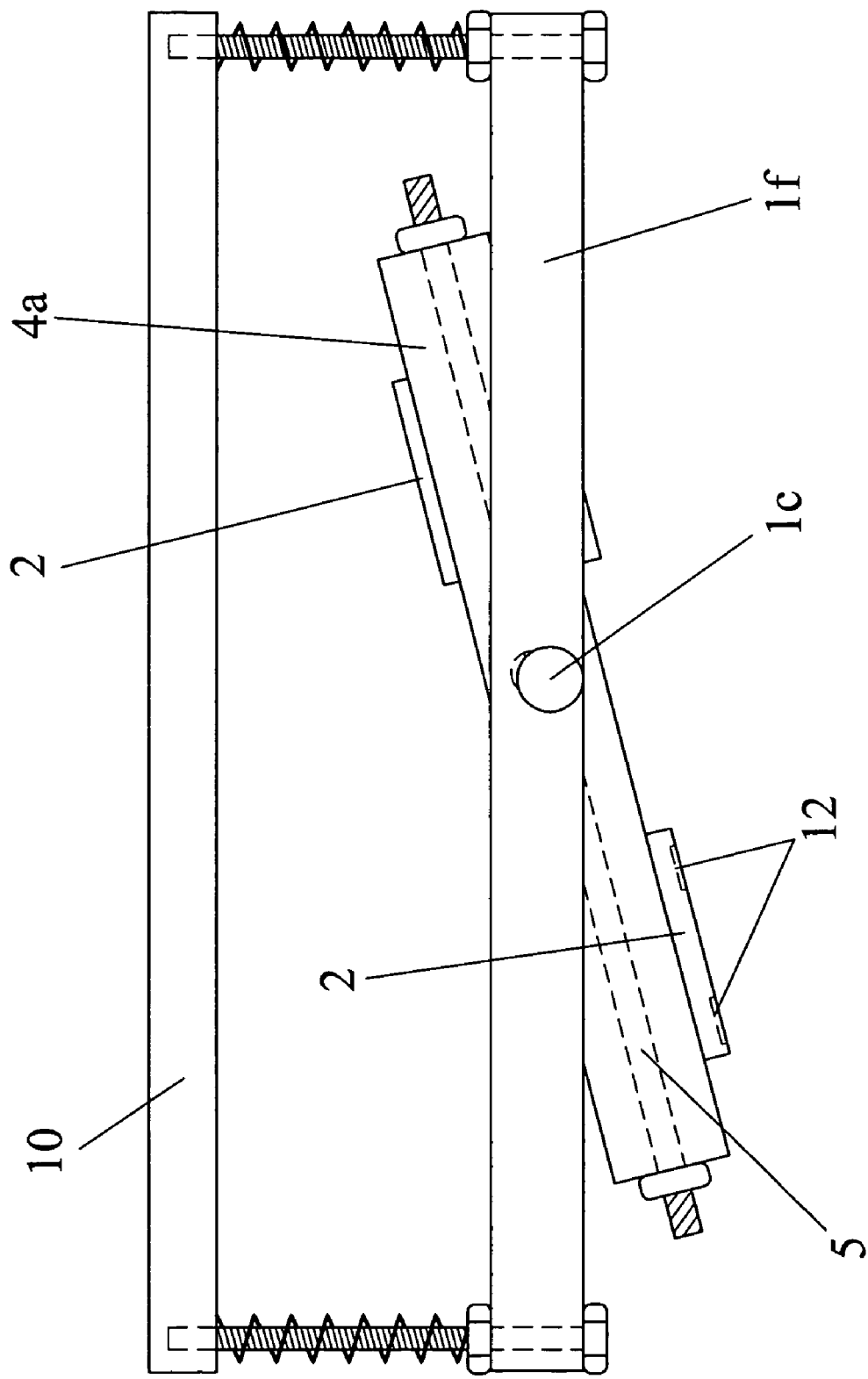
FIG. 4 is a view corresponding to FIG. 3 but in which the tilting frame is tilting in a different position from that shown in FIG. 3.

FIG. 4 illustrates this first embodiment such that the tilting frame 4 is tilting around the main tilting axis 1c in a different position from that shown in FIGS. 1, 2 and 3.

In a second embodiment of the invention, the tilting frame 4 comprises a central cross-member 4g parallel to the main tilting axis 1c separating the central opening 4h presented by that tilting frame 4 into a first part of the central opening 4e on one side of the central cross-member 4g and a second part of the central opening 4f on a second side of said central cross-member 4g.

In this second embodiment, at least one feeler-carrier device 2 is located in the first part of the central opening 4e in at least one axis of rotation 5a transverse to the main tilting axis 1c, and at least one feeler-carrier device 2 is located in the second part of the central opening 4f in at least one axis of rotation 5b transverse to the main tilting axis 1c, said axes of rotation 5a, 5b extending between the central cross-member 4g and the end cross-members 4c and 4d respectively.

Figure 5:
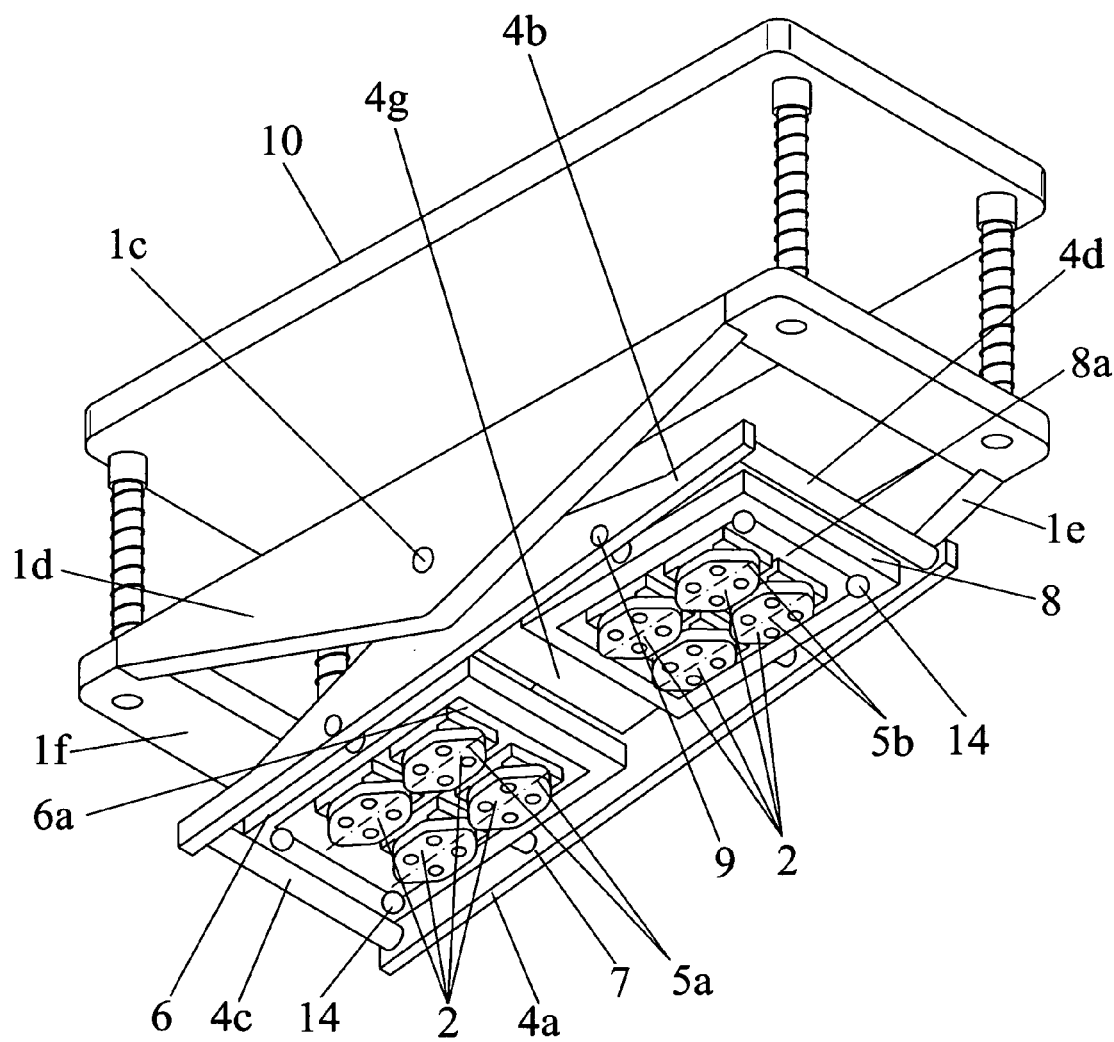
FIG. 5 is a diagrammatic view in lower perspective of a head in accordance with a second embodiment of the invention.
Figure 6:
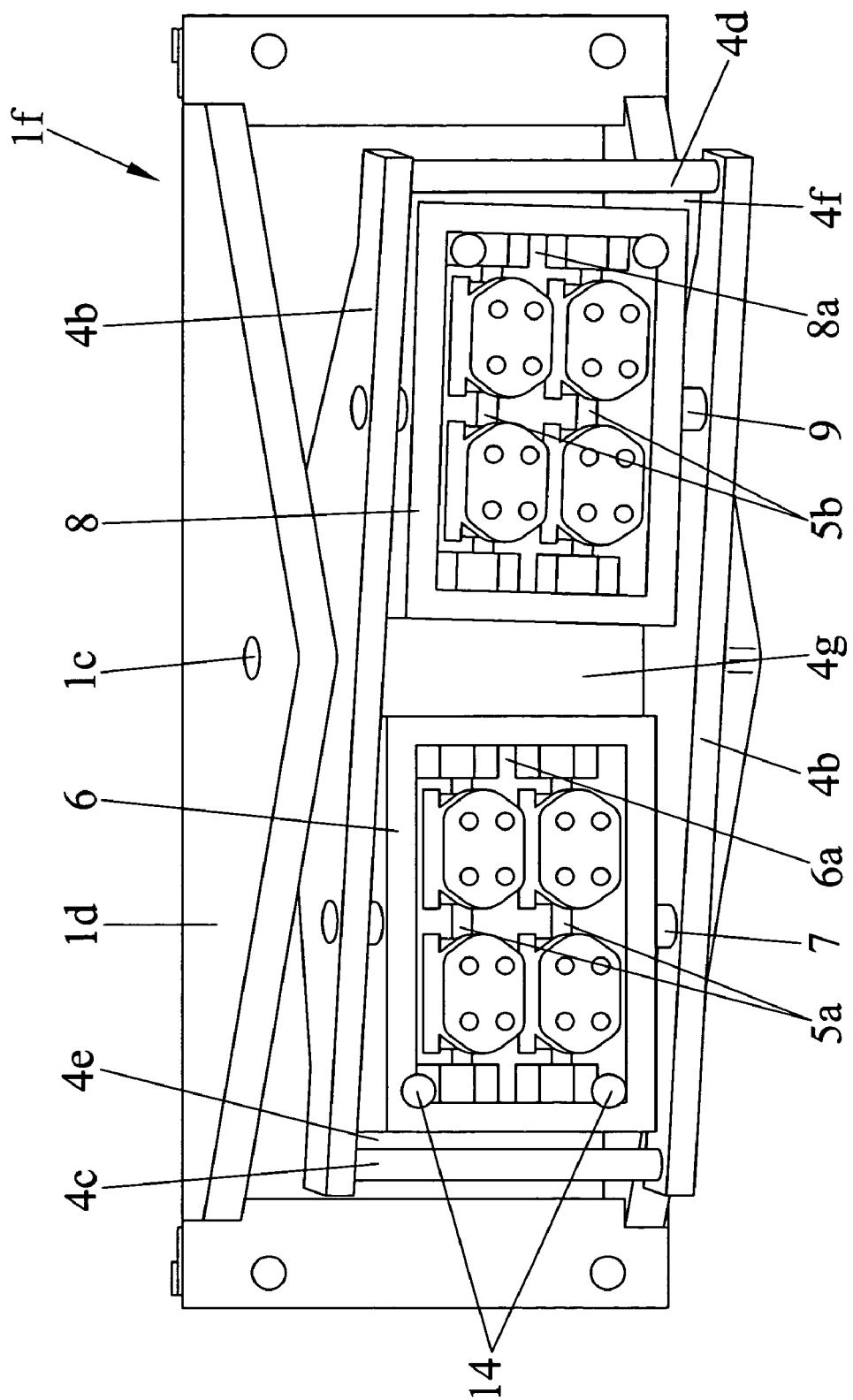
FIG. 6 is a diagrammatic view in lower perspective of the tilting frame and of the lower base of the head shown in FIG. 5.
Figure 7:
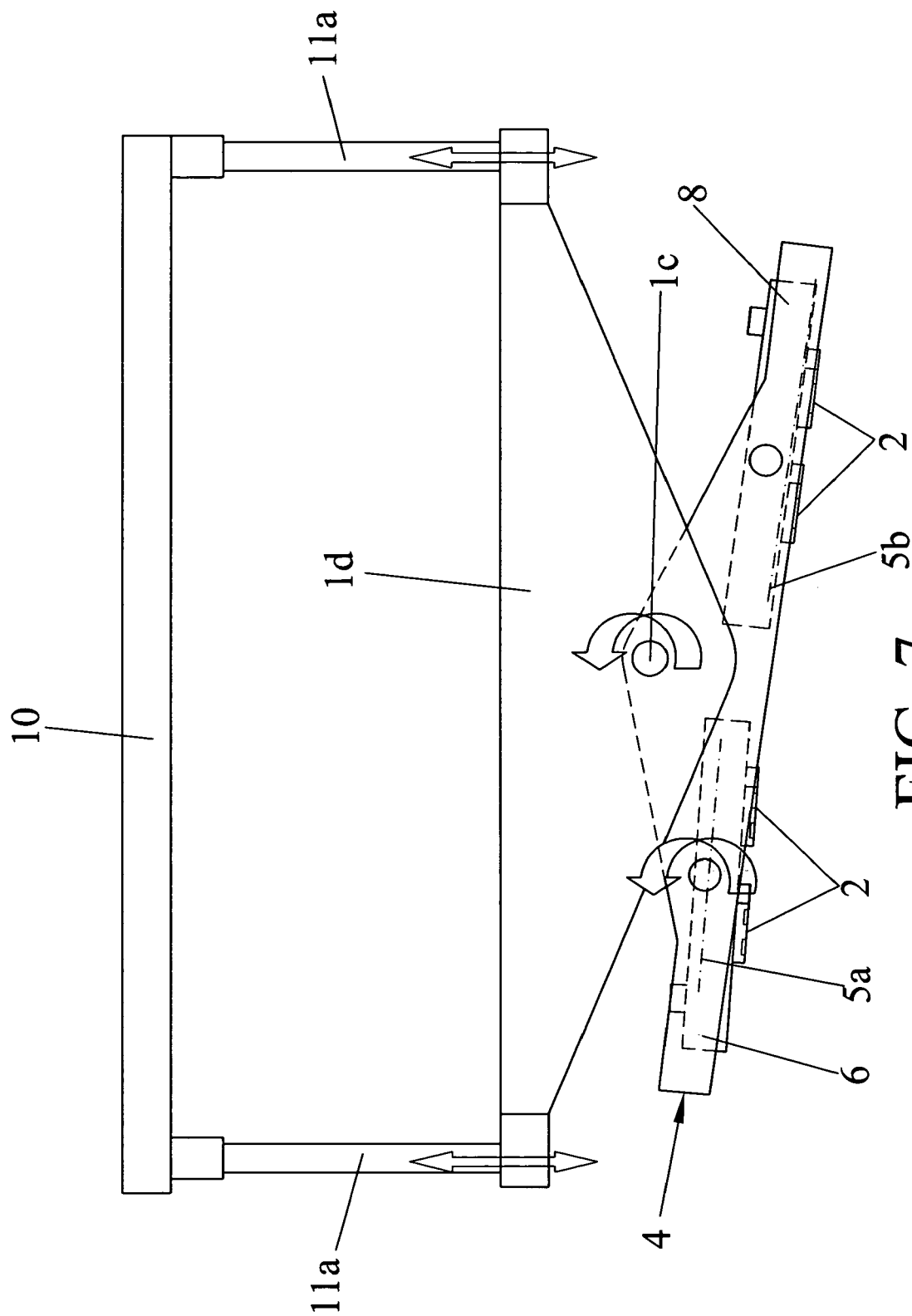
FIG. 7 is a lateral diagrammatic view of the head shown in FIG. 5.

FIGS. 5, 6 and 7 show a preferred embodiment of the invention in which, as can be seen in those figures, each of the said first part of the central opening 4e and second part of the central opening 4f house secondary tilting frames, a first secondary tilting frame 6 and a second secondary tilting frame 8, each joined to the tilting frame 4 by two opposite points in the same way as the tilting frame 4 is joined to the first lower base 1f, and defined between those opposite points are separate secondary axes respectively, a first secondary tilting axis 7 and a second secondary tilting axis 8, both secondary tilting axes being parallel to the main tilting axis 1c, and both secondary tilting axes being located between the side-members 4a, 4b. So, in the same way as the tilting frame 4 rotates around the main tilting axis 1c, the first secondary tilting frame 6 and the second secondary tilting frame 8 rotate around the first secondary tilting axis 7 and the second secondary tilting axis 8, respectively, in a manner independent from the rotation of the first tilting frame 4, and also independent of each other.

The advantage of this embodiment compared to the embodiment with a single frame is the greater adaptability to the curvature of the surface to test, since in this case the feeler-carrier devices adapt themselves to the surface thanks to the rotation of the tilting frame 4 together with the independent rotations of the first secondary frame 6 and the second secondary tilting frame 8, in addition to the actual rotary movement of the feeler-carrier devices 2 around their axes of rotation 5a, 5b.

In said preferred embodiment, the first point of rotation 1a and the second point of rotation 1b are respectively located in a first plate 1d and a second plate 1e, which emerge vertically from the opposite side-members of the first lower base. In this case, as can be seen in FIGS. 5, 6 and 7, the first plate 1d and the second plate 1e present a substantially inverted triangular shape, in such a way that the main tilting axis 1c is arranged between said first plate 1d and said second plate 1e, in a zone close to the free lower vertex of the plates.

The advantage of this arrangement of the plates in a triangular shape is that it facilitates the rotation of the tilting frame 4 around the main tilting axis 1c and therefore the examination of surfaces with greater variation in height owing to greater curvatures or greater irregularities.

In any of the embodiments, the chassis 1 comprises a second lower base 10 which permits it to couple to the displacement system 3, such as for example a numerical control machine. The first lower base 1f is coupled to said second lower base 10 via the adjustment elements 11 which permit the distance between the first lower base 1f and the second lower base 10 to be adjusted. Thanks to the possibility of being able to adjust the distance between the two bases, the head has a certain degree of freedom of vertical movement so that, in order to locate the feelers on the piece to test, the displacement system 3 regulates the necessary height according to the surface and curvature of that piece and it is the adjustment elements 11 which manage to absorb the differences that might exist between the model of the piece and the real piece.

Figure 8:
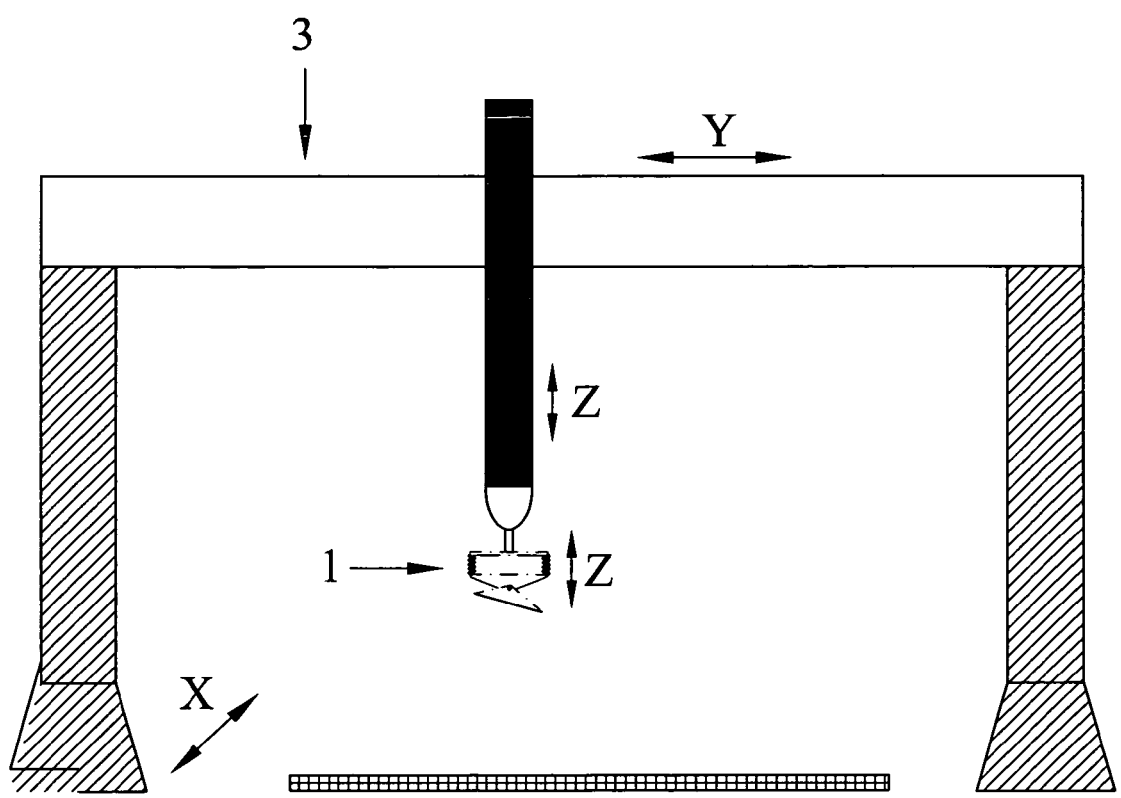
FIG. 8 is a diagrammatic view of the displacement system together with the head forming the object of the invention.

FIG. 8 shows in diagrammatic form the union between the ultrasonic head and the displacement system 3 and their possible movements.

FIGS. 2, 3, 4, 5 and 7 show an embodiment of the union of the first lower base 1f and the second lower base 10, along with a preferred embodiment of the adjustment elements 11. As can be seen in the figures, said adjustment elements 11 comprise a set of springs 11c which are located on rods 11a. Said rods join the first lower base 1f with the second lower base 10, being introduced into a set of holes 11b made in those bases.

FIG. 1 shows a preferred embodiment of the feeler-carrier device. In that embodiment, each one of the feeler-carrier devices comprises means of adjustment in height 18. Said means of adjustment in height 18 are springs. They permit small vertical adjustments, less than those permitted by the springs 11c of the adjustment elements 11 of the first lower base 1f with the second lower base 10, thereby allowing small variations in height or minor irregularities to be overcome and providing an adequate adaptability of the feelers 12 to the surface of the piece to examine.

Figure 9:
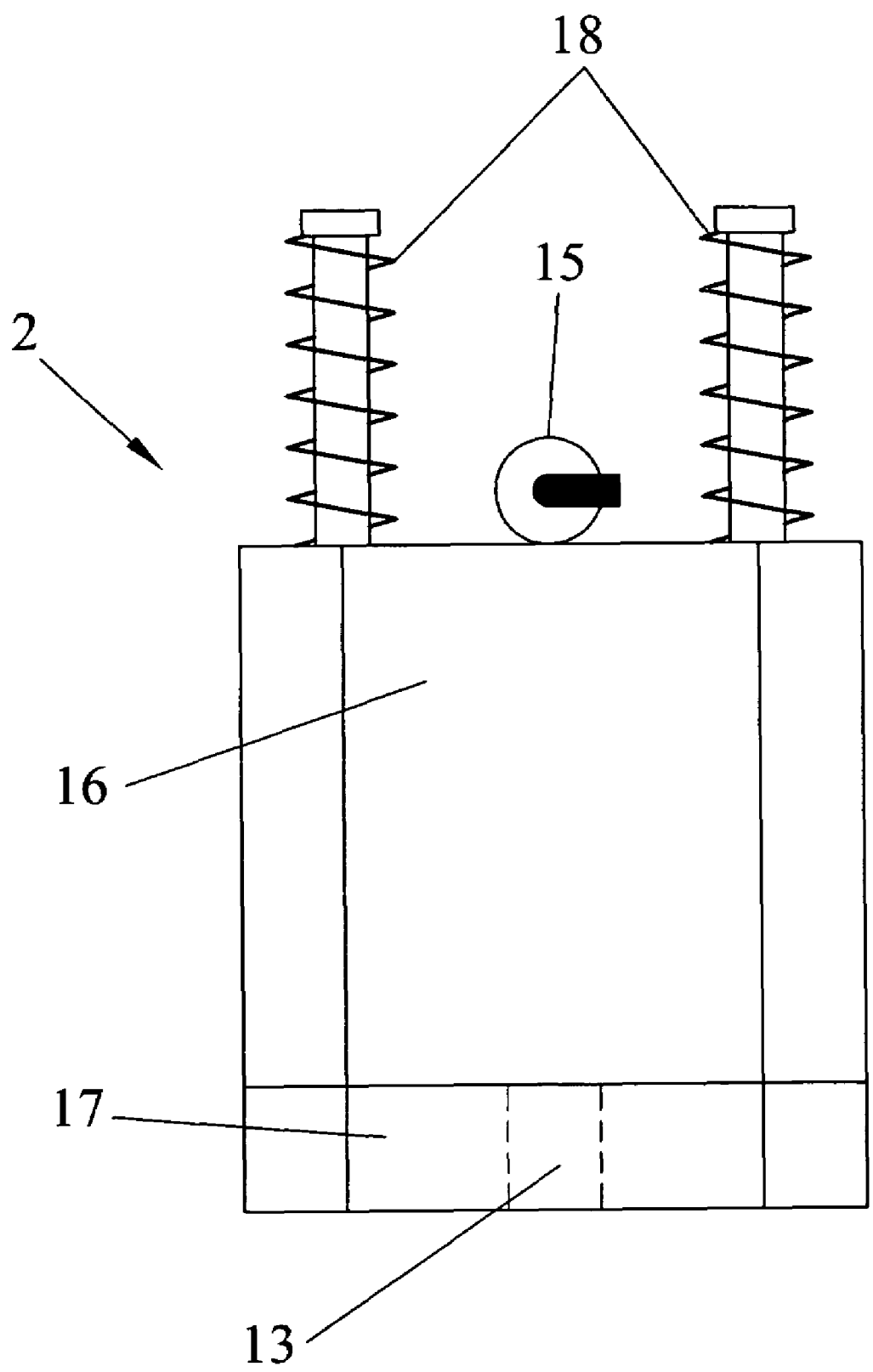
FIG. 9 is a diagrammatic view of the feeler-carrier.

In FIG. 9 a preferred embodiment can be seen of the feeler-carrier device 2. In it, said feeler-carrier device 2 is divided into two parts, an upper part of the feeler-carrier 16 and a lower part of the feeler-carrier 17. Said lower part of the feeler-carrier 17 can be replaced by a new one when that lower part 17 becomes worn due to friction occasioned during the displacement of the feeler-carrier 2 over the surface to test. Said upper part 16 and said lower part 17 are joined by means of an attachment element 13.

In FIG. 9 can also be seen the inlet means of the coupling medium, in this case water, for a proper transmission of the ultrasonic waves. Said water inlet means provide the water needed for the correct transmission of the ultrasonic waves. In a preferred embodiment, said water inlet means consist of an inlet duct for water provided in each of the feeler-carrier devices.

Any of the embodiments shown can present an array of end-of-piece detection sensors 14. Said sensors 14 are located in the periphery of the tilting frame 4 in the event that the embodiment has just the said tilting frame 4 or in the periphery of the first secondary tilting frame 6 and of the second secondary tilting frame 8 in the event that the invention is embodied with said secondary frames in addition to the tilting frame 4. Said detection sensors detect the end of the piece, preventing the head from departing from the piece in its examination movement. These sensors 14 can be removed so that they can be used or not depending on the need.

The invention claimed is:

1. Ultrasonic head for pulse-echo multichannel inspection applied to flat and curved surfaces, which comprises
    a chassis, housing an array of feeler-carrier devices each one carrying at least one ultrasonic feeler and which can be coupled to a displacement system which permits the head to be displaced over the entire surface of curved and flat pieces to inspect by means of ultrasonic sweeping using a coupling medium between the head and the piece to test,
    wherein
    the chassis comprises a first point of rotation and a second point of rotation between which is defined a main tilting axis, and a tilting frame coupled to the chassis via said first point of rotation and said second point of rotation in such a way that said tilting frame rotates around the main tilting axis, and said tilting frame defines a central opening and
    at least one feeler-carrier device is located in said central opening in at least one axis of rotation transverse to the main tilting axis of the tilting frame.

2. Head according to claim 1, wherein said chassis comprises a first lower base, and the first point of rotation and the second point of rotation are to be found in opposite points of that first lower base which surrounds at least a portion of the tilting frame.

3. Head according to claim 2, wherein the tilting frame has a substantially rectangular shape and comprises a first side-member and a second side-member perpendicular to the main tilting axis, joined together respectively by a first end cross-member and a second end cross-member, parallel to the main tilting axis, and the first lower base presents a substantially rectangular shape and the first point of rotation and the second point of rotation are to be found in opposite points located in opposite side-members of that first lower base, with at least the first side-member and a second side-member of the tilting frame surrounding said first lower base.

4. Head according to claim 3, wherein the tilting frame comprises a central cross-member parallel to the main tilting axis which separates that central opening into a first part of the central opening located in a first side of the central cross-member and a second part of the central opening located in a second side of the central cross-member.

5. Head according to claim 3, wherein the first point of rotation and the second point of rotation are arranged in a first plate and a second plate respectively, which emerge vertically from said side-members opposite to the first lower base.

6. Head according to claim 4, wherein at least one feeler-carrier device is located in said first part of the central opening in at least one tilting axis transverse to the main tilting axis, and at least one feeler-carrier device is located in said second part of the central opening in at least one tilting axis transverse to the main tilting axis, and each tilting axis extends from between said central cross-member and one of the said end side-members.

7. Head according to claim 5, wherein
    the tilting frame comprises a first secondary tilting frame provided in a first secondary tilting axis and located between the side-members in a zone of the first part of the central opening between the central cross-member and the first end cross-member, and a second secondary tilting frame provided in a second secondary tilting axis and located between the respective side-members in a zone of the second part of the central opening between central cross-member and the second end cross-member;
    the first secondary tilting axis and the second secondary tilting axis are parallel to the main tilting axis;
    the first secondary frame tilts in said first part of the central opening around said first secondary tilting axis and comprises a first secondary opening;
    the second secondary frame tilts in said second part of the central opening around said second secondary tilting axis and comprises a second secondary opening;
    the axis of rotation in which each feeler-carrier device is provided is located in the first secondary frame in said first part of the central opening, and is extended by said first secondary opening; and
    the axis of rotation in which each feeler-carrier device is provided is located in the second secondary frame in said second part of the central opening, and is extended by said second secondary opening.

8. Head according to claim 2, wherein said chassis comprises a second lower base and the first lower base is coupled to said second lower base via some adjustment elements which permit the distance between said first lower base and second lower base to be adjusted, and in that the said second lower base can be coupled to the displacement system.

9. Head according to claim 8, wherein the adjustment elements comprise a set of springs on some rods which are introduced in a set of holes made in said first lower base and second lower base in such a way that they permit the distance between said first lower base and second lower base to be varied, permitting the vertical movement of first lower base with respect to the second lower base.

10. Head according to claim 5, wherein the first plate and second plate present a substantially triangular shape, and in that the main tilting axis is arranged between said first plate and said second plate in a zone close to the respective free vertices of said first plate and said second plate.

11. Head according to claim 1, wherein the feeler-carrier devices comprise means of adjustment in height of the feeler-carrier in such a way that they permit the vertical movement of the feeler-carriers as an additional means for adjusting said feeler-carriers to the variations in height of the surface to test, with contact at all times being maintained between the feelers contained in said feeler-carrier and said surfaces to test.

12. Head according to claim 11, wherein said means of adjustment in height of the feeler-carrier consist of feeler springs.

13. Head according to claim 1, wherein said tilting frame comprises in its periphery a set of end-of-piece detection sensors.

14. Head according to claim 7, wherein said first secondary tilting frame and second secondary tilting frame comprise in their periphery a set of end-of-piece detection sensors.

15. Head according to claim 13, wherein said end-of-piece detection sensors are removable.

16. Head according to claim 1, wherein said feeler-carrier comprises an upper part of the feeler-carrier and a lower part of the feeler-carrier, said lower part being replaceable, and said upper part and said lower part being joined by an attachment element.

17. Head according to claim 1, wherein the coupling medium is water provided by water inlet means.

18. Head according to claim 17, wherein the water inlet means is a set of water inlet ducts arranged in the upper part of the feeler-carrier.

* * * * *